United States Patent [19]

Patton et al.

[11] Patent Number: 4,886,507
[45] Date of Patent: Dec. 12, 1989

[54] Y CONNECTOR FOR ANGIOPLASTY PROCEDURE

[75] Inventors: William E. Patton; William J. Lindsey, both of Dublin, Ohio

[73] Assignee: Medex, Inc., Hilliard, Ohio

[21] Appl. No.: 150,778

[22] Filed: Feb. 1, 1988

[51] Int. Cl.⁴ .......................................... A61M 25/00
[52] U.S. Cl. ................................. 604/284; 128/344
[58] Field of Search .............. 604/283, 284, 165, 166, 604/167, 169, 158, 256; 128/344, 348.1

[56] References Cited

U.S. PATENT DOCUMENTS

| | | |
|---|---|---|
| 4,254,773 | 3/1981 | Waldbillig . |
| 4,311,137 | 1/1982 | Gerard ................................ 604/284 |
| 4,424,833 | 1/1984 | Spector et al. . |
| 4,430,081 | 2/1984 | Timmermans . |
| 4,626,245 | 12/1986 | Weinstein . |
| 4,682,981 | 7/1987 | Suzuki et al. ....................... 604/283 |
| 4,723,550 | 2/1988 | Bales et al. . |
| 4,726,374 | 2/1988 | Bales et al. . |
| 4,769,017 | 9/1988 | Fath et al. ........................... 604/283 |
| 4,781,702 | 11/1988 | Herrli ................................... 604/284 |

Primary Examiner—John D. Yasko
Attorney, Agent, or Firm—Wood, Herron & Evans

[57] ABSTRACT

A connector has a main passage through which a dilatation catheter passes. Combined Tuohy-Borst valve and membrane seals are provided in the main passage to seal the catheter and main passage against flow-by.

6 Claims, 2 Drawing Sheets

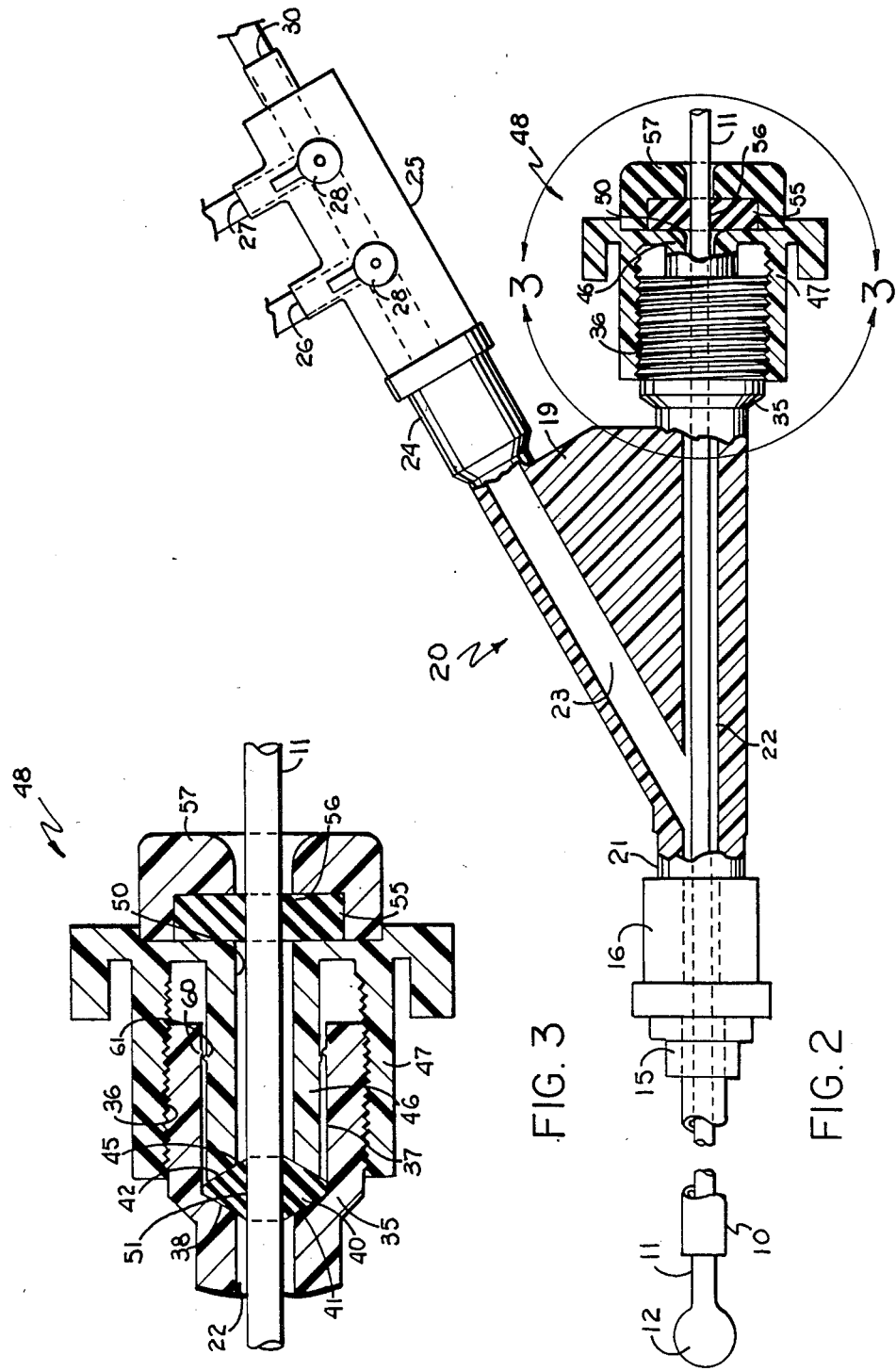

4,886,507

Y CONNECTOR FOR ANGIOPLASTY PROCEDURE

BACKGROUND OF THE INVENTION

This invention relates to a Y connector for use in an angioplasty procedure.

The angioplasty procedure for repair of a blood vessel has been known for many years. The procedure provides an opportunity to open up a clogged blood vessel, particularly a coronary artery, and thus avoid the expense and trauma of bypass surgery.

The procedure involves the insertion of a large guide catheter up to the blood vessel to be repaired. A Y connector is attached to the free end of the guide catheter by means of a rotatable coupling of the type disclosed in U.S. Pat. No. 4,254,773. The Y connector has a main passage through which the dilatation catheter is inserted. The Y connector has a branch passage to which a multiport manifold is connected. One port of the manifold is connected to a blood pressure monitor of the type disclosed in copending application Ser. No. 07/072,909, filed July 14, 1987. Another port of the manifold is connected to a supply of contrast media which is a fluid injected into the blood vessel enabling a real time observation of the blood vessel through X-ray.

At a minimum, the angioplasty procedure involves the following steps:

The guide catheter is inserted through a blood vessel in the patient's arm or leg into the heart.

A blood pressure monitor is connected to the Y connector to provide a continuous monitor of a patient's blood pressure.

The contrast medium is introduced into the blood vessel so that the blockage of the blood vessel can be identified.

A dilatation catheter having a balloon on its free end is introduced through the main passage of the Y connector. When the end of the dilatation catheter is in place in the area of the blockage caused by a growth of placque, a saline mixture is injected through the dilatation catheter to the balloon on its end to inflate it. As the balloon is inflated, it ruptures the placque in the coronary artery so as to permit normal or at least improved blood flow.

The dilatation catheter is thereafter removed and contrast medium again introduced and a post dilatation arteriogram is made to check the success of the procedure.

Thereafter, the dilatation catheter may be reintroduced. It may be desired to use a larger catheter. It may be desired to introduce a small guide wire instead of a dilatation catheter.

In any event, more than one insertion and withdrawal through the main passageway is normally required to complete the angioplasty procedure.

Blood under normal body pressure is of course in the main passageway just as it is in the branch passageway where it is being continuously monitored. The blood will tend to escape through the main passageway as by directly flowing through the main passageway when a catheter is removed or by flowing by the catheter when it has been inserted.

It is known in the prior art to provide sealing against the escape of blood through the main passageway of the Y connector. One seal is an adjustable Tuohy-Borst type valve. The Tuohy-Borst valve includes an O-ring-type element seated in a socket forming part of the main passage. A cap threaded on the end of the passage contains a spigot which compresses the O-ring when the cap is rotated to drive the spigot inwardly. The compression closes down the opening in the O-ring around the catheter to prevent "flow-by." When the catheter is absent, the O-ring can be closed down enough to completely close off the opening in the main passage.

An alternative form of seal employs a membrane having a small hole of about 0.045" diameter. Catheters of a slightly larger outside diameter than the hole are inserted through the membrane, the membrane forming the seal against "flow-by."

Neither Y connector seal is completely satisfactory. The Tuohy-Borst has the disadvantage that it requires manipulation in order to match the size of the opening in the ring to the outside diameter of the dilatation catheter. If the cardiologist does not tighten it sufficiently, blood will flow by the valve. If it is too tight, the catheter can be inserted only with difficulty because of the friction or the catheter can be crushed.

The membrane-type seal eliminates the foregoing disadvantages of the Tuohy-Borst valve but has its own disadvantages. It cannot be completely closed off when a catheter is removed. Under those circumstances, when the dilatation catheter is removed, the Y connector has to be removed and the manifold connected directly to the rotator. During this step, there is nothing to prevent the blood from flowing through the guide catheter and into the surgical area. Further, the smaller catheters, for example 0.036" O.D., cannot properly be sealed by a membrane that has a hole that is 0.045" diameter.

BRIEF SUMMARY OF THE INVENTION

It is an objective of the invention to provide an improved seal for the Y connector, the improved seal eliminating the disadvantages of the Tuohy-Borst and membrane-type seals of the prior art.

More specifically, it is an objective of the invention to provide a seal which permits insertion of the dilatation catheter without need for manipulation of the connector to effect the seal and which precludes blood flow-by; and which permits all steps of the procedure to be performed without requiring the disconnection of the Y connector.

The objects of the present invention are attained by providing a Y connector having, in the main passage, a socket that receives a Tuohy Borst O-ring, a cap with a spigot projecting from it, the cap being threaded onto the outside surface of the socket so that it can be screwed down to bring the spigot into contact with the Tuohy-Borst ring to compress it. The cap has sealed into it a membrane having a 0.040" to 0.035" diameter opening for receipt of a catheter. The spigot and socket are provided with projecting and interfering collars or rims that limit the axial movement of the spigot out of the socket. The limitation is such that when the collars are touching, the spigot is in engagement with the Tuohy-Borst ring to hold it in sufficient compression to block flow of blood around the external surface of the ring, that is, between the ring and the socket. This relationship is important to maintain a seal against flow-by when the membrane is used for the seal. In the prior art, the cap containing the membrane is solvent-sealed to the connector. Such a seal is ruled out when it is necessary to have the threaded connection for a Tuohy-Borst-type operation. Therefore, the combination provides a seal for the membrane-type procedure that does not require the solvent sealing.

The combination as described permits or facilitates a number of procedures that have heretofore not been possible with any Y connector. The dilatation catheter can be inserted through the membrane and no manipulation is required to effect the seal between the membrane and the catheter. The catheter can be removed and blood flow through the main passage blocked by tightening down on the Tuohy-Borst ring to close it completely. The membrane-type seal is available without solvent-sealing of the membrane-containing cap to the connector, the external surface of the Tuohy-Borst ring providing the seal against flow-by. An undersized catheter or thin wire can be used even though its outside diameter would be smaller than the I.D. of the membrane, for in this situation, the Tuohy-Borst valve could be tightened. Thus, the full range of catheters and guide wires is available with the single connector. There never would be a requirement for removal of the connector and reconnecting the manifold to the guide catheter as is the case with some procedures using the membrane. The need for a precise sealing adjustment as is required in the Tuohy-Borst valve is eliminated for all but the smallest catheters. The possibility of air embolism that can occur when the connector is removed and the manifold attached to the guide catheter and vice versa is eliminated.

All of the foregoing objects, features and advantages of the invention will become more readily apparent from the following detailed description taken in conjunction with the accompanying drawings in which:

FIG. 2 is a cross-sectional view of the Y connector; and

FIG. 3 is an enlarged fragmentary view of the encircled portion of FIG. 2.

Figure 1:
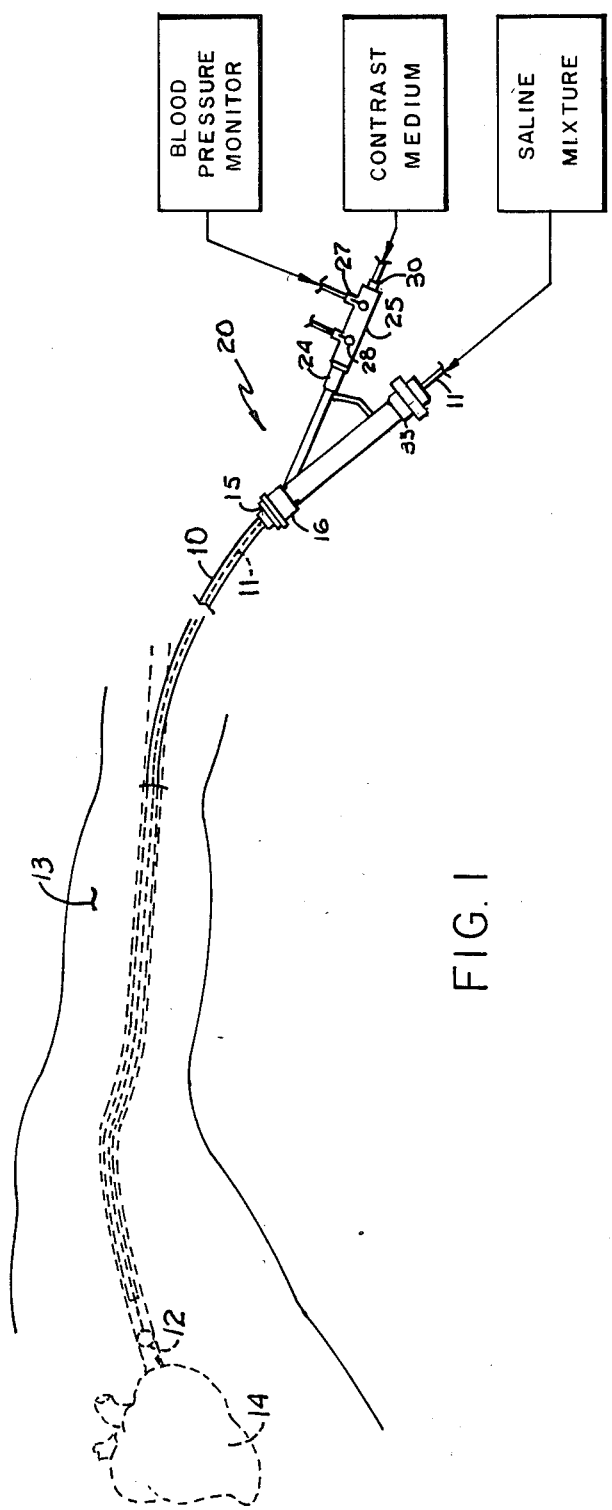
FIG. 1 is a diagrammatic view of the apparatus for performing an angioplasty procedure.

Referring to FIG. 1, a guide catheter 10 is inserted, via a patient's arm or leg 13, into the heart 14 adjacent the coronary artery. A dilatation catheter 11 is positioned inside the bore of the guide catheter. At the end of the dilatation catheter is a balloon 12 which is inflatable by the injection of a saline-based solution.

The guide catheter 10 has a hub 15 that is connected to a rotatable coupling 16 of the type disclosed in U.S. Pat. No. 4,254,773. A Y connector 20 is formed by a clear plastic casing 19 that has a standard male Luer slip 21 which is inserted into the end of the rotator coupling 16.

The Y connector has a main passage 22 and a branch passage 23. The branch passage terminates in a standard female Luer lock 24. A manifold 25 is connected by way of the Luer lock to the branch passage 23. The manifold has at least two ports 26 and 27 that are controlled by stopcocks 28. One port, 27, for example, is connected to a blood pressure monitor of the type described in patent application Ser. No. 07/072,909, filed July 14, 1987. The manifold has another port 30 which is connected to a supply of contract medium that is to be inserted into the coronary artery to provide the contrast for an arteriogram that is used throughout the procedure.

The main branch 22 has a socket 35 which is threaded as at 36 on its external surface. As seen in FIG. 3, the socket has an internal surface 37 having a tapered valve seat 38 at one end. A silicon or rubber O-ring 40 is seated at the bottom of the socket against the tapered seat 38. The cross section of the O-ring 40 is trapezoidal. One surface 41 of the trapezoid sits on the seat 38. The other surface 42 of the trapezoid is engaged by a frustoconical surface 45 at the end of a spigot 46. The O-ring has a circular opening which, in a relaxed condition, is about 0.080 inch.

The spigot 46 is integral with a skirt 47 that surrounds the socket 35 and has internal threads by which it is threaded onto the threads 36 of the socket. The spigot and skirt form a closure 48. By rotating the spigot assembly on the socket, the spigot 46 will move axially toward and away from the flexible O-ring 40 to compress it or relieve the pressure against the seat 38, thus creating a Tuohy-Borst-type valve.

The spigot has a bore 50 which is coaxial with the main passageway 22 and a bore 51 through the O-ring 40. At the outer or proximal end of that bore 50 is a membrane 55 having a tiny bore 56 of 0.040" to 0.035" diameter which grips the catheter 11 and forms a seal with it. The membrane 55 is retained on the closure 48 by means of a cap 57 that is ultrasonically welded to the spigot assembly to form a leak-tight seal with the spigot assembly.

The socket 35 has an inwardly-directed collar 60 and the spigot 46 has an outwardly-directed collar or rim 61. When the spigot 46 is inserted into the socket far enough to slightly compress the soft ring 40 on the seat 38, the collar 61 is in engagement with the collar 60, thus defining the outer limit of movement of the spigot with respect to the socket. As long as the spigot goes no farther outward with respect to the socket, the seal against flow-by will always be maintained by the compression of the ring 40 against the seat 38 and the surface 42.

During a procedure, the dilatation catheter 11 passes through the main passageway 22, the bore 51 in the O-ring, the bore 50 in the spigot, the bore 56 in the membrane and out of the proximal end of the Y connector. The free end of the dilatation catheter is connected to a supply of a saline mixture by which the balloon 12 in the dilatation catheter is inflated.

In operation, the guide catheter is connected to the Y connector and the manifold with its attachments are attached to the Y connector. The guide catheter is inserted via the patient's arm or leg into the patient's coronary artery. As it is snaked through that tortuous path, the rotator 16 permits it to twist while the Y connector and its attachments remain in a relatively fixed position.

With the guide catheter in place, the contrast medium is inserted through the port 30 and the branch passageway 23. With the contrast medium in the coronary artery, an arteriogram shows the cardiologist the area of blockage.

The dilatation catheter is then inserted into the coronary artery with the balloon 12 positioned within the area of blockage. Possibly preliminary to the insertion of the dilatation catheter, a small guide wire will have to be inserted in order to open the blocked artery sufficiently to permit the introduction of the balloon catheter. As the dilatation catheter passes through the membrane 55, it is sealed with respect to the membrane and blood is prevented from exiting the Y connector via the membrane. Blood is also prevented from flowing between the spigot and socket surfaces by the slight compression of the O-ring 40 against the seat 38 and the frustoconical surface 45 on the spigot.

As long as collar 61 has not moved outwardly past the collar 60, the seal against flow-by at the rubber seal 40 will remain intact.

Once the dilatation catheter is in place, it is gradually inflated to rupture the placque that is creating the blockage of the coronary artery. The catheter is thereafter withdrawn. When it is withdrawn, blood will want to exit through the membrane 50. However, by turning down the spigot onto the Tuohy-Borst valve, the valve can be completely closed down, thereby blocking flow of blood out of the main passage 22.

With the catheter removed, contrast medium is again injected and an arteriogram is viewed to determine the success of the procedure thus far.

It may be determined that a larger dilatation catheter should be inserted. If so, that operation is performed by partially inserting the catheter up to the Tuohy-Borst valve, opening the Tuohy Borst valve and proceeding with the insertion of the catheter. The inflation procedure is repeated.

If it is desired to use a catheter or wire smaller than the 0.040" to 0.035" bore in the membrane 55, the leakage can be blocked by the turning down of the Tuohy-Borst valve, care being exercised to prevent the crushing of the small catheter or imparting such a great friction to it or the wire that it cannot be threaded into the artery.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof.

We claim:

1. A Y-connector for an angioplasty procedure comprising,
   a casing having a bore forming a main passageway for a catheter and having a branch passageway intersecting the main passageway,
   a Tuohy-Borst valve in the main passageway,
   and a membrane disposed in said main passageway,
   said membrane being coaxial with and spaced from said Tuohy-Borst valve,
   said membrane having a small hole for receiving a dilatation catheter.

2. A Y-connector for an angioplasty procedure comprising,
   a casing having a bore forming a main passageway for a catheter and having a branch passageway intersecting the main passageway,
   a first seal in said main passageway having a circular opening therethrough,
   means for adjusting the diameter of said opening to any diameter between about 0.050 inch and zero,
   and a second elastomeric seal in said main passageway having a fixed circular opening having a diameter in the range of about 0.040 to 0.035 inch,
   said second seal preventing blood flow by a dilatation catheter inserted in said passageway, said first seal being adapted to close said passageway when a catheter is removed.

3. A connector as in claim 2 further comprising,
   a closure on said passageway at one end of said casing,
   said second seal being mounted on said closure,
   said closure being threaded onto said casing,
   a spigot on said closure projecting into passageway and in contact with said first seal, said spigot being operative to close the opening in said seal when moved toward said seal by rotating said closure.

4. A connector as in claim 3 in which said first seal provides a seal against flow of fluids between the outside of said spigot and said casing.

5. A connector as in claim 4 further comprising, detent means limiting axial movement of said closure and spigot away from said first seal whereby to maintain pressure of said spigot on said first seal.

6. A Y-connector for an angioplasty procedure comprising,
   a casing having a bore forming a main passageway for a catheter and having a branch passageway intersecting said main passageway,
   a shoulder forming a seat in said main passageway,
   a compressible O-ring on said seat,
   a closure at one end of said passageway and threaded on said casing,
   a spigot on said closure extending into said passageway to compress said O-ring against said seat and to prevent fluid flow between the outside of said spigot and said casing,
   said spigot adapted, upon screwing down said closure, to close said O-ring,
   a membrane in said closure spaced from and axially aligned with said O-ring,
   said membrane having a circular opening about 0.040 inch in diameter to receive and seal a catheter,
   and detent means between said spigot and passageway to restrict movement of said spigot away from said O-ring and thus to maintain said O-ring always under some compression.

* * * * *